(12) United States Patent
Flitcroft

(10) Patent No.: US 7,976,162 B2
(45) Date of Patent: Jul. 12, 2011

(54) EYE EXAMINING SYSTEM AND METHOD

(76) Inventor: Daniel Ian Flitcroft, Rathmichael (IE)

( * ) Notice: Subject to any disclaimer, the term of this patent is extended or adjusted under 35 U.S.C. 154(b) by 17 days.

(21) Appl. No.: 12/441,271

(22) PCT Filed: Sep. 26, 2006

(86) PCT No.: PCT/EP2006/066940
§ 371 (c)(1),
(2), (4) Date: Mar. 13, 2009

(87) PCT Pub. No.: WO2008/037299
PCT Pub. Date: Apr. 3, 2008

(65) Prior Publication Data
US 2009/0303435 A1 Dec. 10, 2009

(51) Int. Cl.
*A61B 3/14* (2006.01)
*A61B 3/10* (2006.01)

(52) U.S. Cl. .................. 351/209; 351/205; 351/211

(58) Field of Classification Search .......... 351/204–206, 351/209–211, 221, 246
See application file for complete search history.

(56) References Cited

U.S. PATENT DOCUMENTS

| 3,364,603 A | 1/1968 | Tate |
| 3,561,146 A | 2/1971 | Dembar |
| 3,598,107 A | 8/1971 | Ishikawa et al. |
| 3,712,716 A | 1/1973 | Cornsweet et al. |
| 3,724,932 A | 4/1973 | Cornsweet et al. |
| 3,804,496 A | 4/1974 | Crane et al. |
| 4,257,688 A | 3/1981 | Matsumura |
| 4,287,410 A | 9/1981 | Crane et al. |
| 4,370,033 A | 1/1983 | Kani et al. |
| 4,373,787 A | 2/1983 | Crane et al. |
| 4,729,652 A | 3/1988 | Effert |
| 5,094,521 A | 3/1992 | Jolson et al. |
| 5,191,897 A | 3/1993 | Meshel |
| 5,757,460 A * | 5/1998 | Cockley ........................ 351/205 |
| 5,838,420 A | 11/1998 | MacGregor Donaldson |
| 6,027,216 A | 2/2000 | Guyton et al. |
| 6,456,261 B1 | 9/2002 | Zhang |
| 2005/0231688 A1 | 10/2005 | Jones et al. |
| 2007/0171363 A1 * | 7/2007 | Chen et al. ................... 351/200 |

FOREIGN PATENT DOCUMENTS

| JP | 11028187 | * | 2/1999 |
| WO | WO-88/05281 | | 7/1988 |

OTHER PUBLICATIONS

Brodie, "Corneal Topography and the Hirschberg test," *Appl Opt*, (1992) 31:3627-3631.
Brodie, "Photographic calibration of Hirschberg test," Invest Ophthalmol Vis Sci, (1987) 28:736-742.
International Search Report and Written Opinion for PCT/EP2006/066940.

(Continued)

*Primary Examiner* — Dawayne A Pinkney
(74) *Attorney, Agent, or Firm* — Scott E. Kamholz; Peter K. Sollins; Foley Hoag LLP

(57) ABSTRACT

The present invention is directed to a system and method of using a hand held occluder, which is visually opaque but transmits infrared light, in combination with an infrared imaging device for measuring deviations of an eye using cornea reflex measurement of a fixation target.

21 Claims, 6 Drawing Sheets

OTHER PUBLICATIONS

Barry et al., "Limbus versus pupil centre for ocular alignment measurement with corneal reflexes," *Invest Ophthalmol Vis Sci*, (1997) 38:2597-2607.

Choi et al., "The accuracy of experienced strabismologist using the Hirschberg and Krimsky tests", *Ophthalmology* (1998) 105:1301-1306.

Guyton et al., "Automated Measurement of Strabismic Deviations Using a Remote Haploscope and an Infrared Television-Based Eye Tracker," *Trans Am Ophthalmol Soc*, (1987) 85:320-331.

Hasebe et al., "Biometric Confirmation of the Hirschberg Ratio (HR) in Strabismic Children", *Invest Ophthalmol Vis Sci*, (1998) 39:2782-2785.

Hasebe et al., "The reliability of a video-enhanced Hirschberg test under clinical conditions," *Invest Ophthalmol Vis Sci*, (1995) 36:2678-2685.

Miller et al., "Videographic Hirschberg measurement of simulated strabismic deviation," *Invest Ophthalmol Vis Sci*, (1993) 34:3220-3229.

* cited by examiner

EYE EXAMINING SYSTEM AND METHOD

Cross-Reference to Related Application

This application is the National Stage of International Application No. PCT/EP2006/066940, filed Aug. Sep. 29, 2006.

INTRODUCTION

The present invention is directed to an eye examining device and a system and method for measuring deviations of an eye using cornea reflex measurement of a fixation light.

Strabismus or squint in an ocular condition which, when an individual attempts to fixate on a target, results in the two eyes of an individual aiming at two different points in space. It is generally caused by, for example, a weakness of one eye muscle.

The fundamental techniques in detecting and measuring strabismus is the cover test or alternate cover test in which each eye is covered in turn with an opaque eye occluder while the subject fixes on a particular object, called the fixation target, and an observer observes any movement of the subject's uncovered eyes.

Another technique is the prism cover test, wherein the observer ultimately covers each eye of the subject, while the subject looks at a fixation target. In this way, one eye is always covered while the fixation target is being viewed. If there is an imbalance in the position of the eye, then the eye under the cover deviates either inwards, an eso-deviation, or outwards, an exo-deviation. When the cover is switched to the other eye, the now deviating eye must move to bring the fixation target back into central vision. The amount of this deviation can be measured by placing prisms of varying powers in front of either eye until there is no movement when the cover is moved from one eye to the other. In this situation, the angle of the deviation is the same as the angular deviation created by the prism which can be measured in either degrees or prism dioptres. The prism cover test also allows the measurement of the combination of the manifest and latent components of a squint.

However, these tests require the subject to be able to maintain fixation with the distraction of an occluder moving continually from one eye to the other. In children, this often makes the test impossible.

Furthermore, these tests only work if each eye has good enough vision to take up fixation of a target when it is uncovered. If vision is reduced in one, as is commonly the case in strabismus due to the co-existence of amblyopia, then this can make the alternate prism test inaccurate or impossible.

A number of additional tests have been described to determine and measure deviations of the eyes from the position on the cornea (relative to the pupil or the edge of the cornea) of the reflection of a fixation light. The brightest visible reflection is from the front surface of the cornea and is often referred to as the corneal reflex or corneal reflection. More accurately this reflection is the first of the four Purkinje images, the second to fourth images being generated by the posterior corneal surface, and the anterior and posterior surfaces of the crystalline lens within the eye respectively. These additional tests which use the Purkinje images include the Hirschberg test, the Prism reflection test and the Krimsky test.

In the Hirschberg Test, the subject is asked to look at source of light with an observer aligned directly behind the light so that the corneal reflections can be seen by the observer. If both eyes are aligned the corneal reflection will be located at the same position in the two eyes. If one eye is deviated due to the presence of strabismus then the corneal reflection in this eye will be seen shifted nasally (inwards) if the eye is deviated outwards (an exo-deviation) or temporally (outwards) if the eye is deviated inwards (an eso-deviation). The amount of displacement of corneal reflection can be used to assess the angle of deviation.

The relationship between the deviation of the corneal reflection and the deviation of the eye is called the Hirschberg ratio. Hasebe et al (Biometric Confirmation of the Hirschberg Ratio (HR) in Strabismic Children. *Invest Ophthalmol Vis Sci.* 1998;39:2782-2785) accurately characterised this relationship and found a mean HR of 19.9 PD/mm (PD=Prism Dioptres). This leads to the equation, $D=5.12 \sin(\theta)$, where D is the displacement of the light reflection from the centre of the pupil (in millimetres), and $\theta$ is the strabismic angle (degrees).

The Prism Reflection or Reflex Test is conducted in a similar manner to the Hirschberg test with the patient fixing on a light while an observer views the corneal reflections. Prisms of varying strength (base-out for an eso-deviation; base-in for an exo-deviation) are placed before the fixing eye. The prism will shift the image of the object towards the apex of the prism as a result the eye behind the prism will move so as to maintain fixation on the object. As the fixing eye moves to maintain fixation the non-fixing eye also moves. When the corneal reflection in the deviating eye is symmetrical to the fixing eye then the angle of deviation will be equal to the power of the prism in front of the fixing eye.

The Krimsky test is a variation of the Prism Reflex Test. Prisms are placed over the deviating eye with prism power chosen to bring the corneal reflection back to the centre of the pupil or back to its position when the deviating eye is fixating. It is harder to accurately assess the corneal reflection position through the prism but there is the advantage that the fixing eye remains in the primary position.

To assess the manifest components of a squint, i.e. that present when both eyes are in use, the tests are preformed with both eyes uncovered (binocular viewing). To include the latent component of a squint one eye is covered (monocular viewing). In some subjects this will reveal a deviation not seen in binocular viewing, in others the manifest angle will be increased. In this latter situation the latent component is the difference between the measurements in monocular and binocular viewing.

These techniques and methods have been described in the ophthalmological literature including Choi R Y, Kushner B J. The accuracy of experienced strabismologist using the Hirschberg and Krimsky tests. *Ophthalmology* (1998) 105:1301-1306, Barry J C, Backes A. Limbus versus pupil centre for ocular alignment measurement with corneal reflexes *Invest Ophthalmol Vis Sci.* (1997) 38:2597-2607, Hasebe S, Hiroshi O, Tadokoro Y, Okano M, Furuse T. The reliability of a video-enhanced Hirschberg test under clinical conditions. *Invest Ophthalmol Vis Sci.* (1995) 36:2678-2685. 4, Miller J M, Mellinger M, Greivenkemp J, Simons K. Videographic Hirschberg measurement of simulated strabismic deviation. *Invest Ophthalmol Vis Sci.* (1993) 34:3220-3229, Brodie S E. Photographic calibration of Hirschberg test. *Invest Ophthalmol Vis Sci.* (1987) 28:736-742 and Brodie S E. Corneal Topography and the Hirschberg test. *Appl Opt.* (1992) 31:3627-3631.

While these standard clinical techniques do not require any specialized apparatus, a range of inventions have been described that aim to improve on various aspects of the measurement of deviations of the eyes.

In particular, U.S. Pat. Nos. 3,712,716, 3,724,932, and 3,804,496 describe the use of two of the Purkinje images to measure eye position. These patents describe an instrument for imaging the first and pair of split-field intensity discriminating photo cells to control a tracking mirror, so as to develop signals indicative of the actual eye movement. Related devices are also shown in U.S. Pat. Nos. 4,287,410 and 4,373,787. Both of these patents use the first and fourth Purkinje images to track eye movements.

U.S. Pat. Nos. 3,598,107, 4,257,688 and 4,370,033 describe the principle of utilizing a light source and a video camera to image the human eye for carrying out various measurements for several different clinical purposes, such as determining light sensitivity distribution over the retina and determination of pupil size.

US Patent application No. 2005/0231688 is directed to the use of night vision infrared capable imaging devices for retinal scanning. This invention deals with avoiding the need to dilate the pupil of a patient when carrying out retinal scanning to allow visualization of the retina within the eye.

U.S. Pat. No. 4,729,652 describes an apparatus for performing measurements on the eye where the first and fourth Purkinje images are used and combined with an infrared filter. To measure the eye position a frame is rotated around the eye until the first and fourth Purkinje images are aligned. The device described in this patent is a complicated apparatus involving the interaction of many components and which also requires that the imaging system is off axis.

Guyton et al (Guyton, D. L., Moss, A., and Simons, K., Automated Measurement of Strabismic Deviations Using a Remote Haploscope and an Infrared Television-Based Eye Tracker, Trans. Am. Ophthalmol. Soc. (1987) 85:320-331) have described an ingenious but complicated form of eye tracker which combines a haploscope with a large convex mirror. The principle problem with this approach is one of complexity followed by the fact that the apparatus does not facilitate viewing fixation targets close up and far away. U.S. Pat. No. 6,027,216 (Guyton et al) describes another approach for measuring the position of the eye using the pattern of polarization of light reflected from the eye. However, these reflections and the associated polarization are derived from the retinal surface only.

The present invention is directed to an improved method for detecting and measuring strabismus which overcomes the disadvantages outlined above.

The present invention addresses the problems associated with these known clinical techniques. These include the problems encountered when making measurements in uncooperative subjects or subjects with poor fixation in one eye for whom a standard clinical test for measuring deviations of the eye are unsuitable.

The present invention also provides a new way to obtain measurements of deviations of an eye in situations where the standard alternate cover test cannot be relied upon.

STATEMENTS OF THE INVENTION

According to the first aspect of the invention, there is provided system for measuring deviations of an eye using corneal reflex measurements of a fixation target wherein the system comprises
a. An infrared light source aligned with or adjacent to a fixation target;
b. A hand held visually opaque infrared transmitting eye occluder; and
c. An infrared imaging device to observe and/or record the eye and corneal reflex measurements.

According a second aspect of the invention, there is provided a method for measuring deviations and observing movements of an eye using corneal reflex measurements comprising the steps of:
a. Directing an infrared light source toward the eye of a subject while the subject looks at a fixation target and wherein the infrared light source is aligned or adjacent to the fixation target;
b. Covering one eye of the subject with a hand held visually opaque infrared transmitting occluder;
c. Observing the changes in the deviation of the occluded eye through the visually opaque infrared transmitting occluder via an infrared imaging device and/or recordal of these changes.

According to a third aspect of the invention, there is provided a visually opaque hand held eye occluder which transmits infrared light and occludes vision through an eye of a subject.

According to a fourth aspect of the invention, there is provided a method for screening eye abnormalities in a group of subjects using the method as described previously and comprising the further steps of obtaining multiple images of the eyes of each subject for analysis at the time of examination and/or for later review.

Advantageously, the present invention allows a combination of the conventional cover test with techniques that determine eye position from the cornea reflex or corneal reflection (CR), i.e. locations of light reflection from the surface of the eye.

Previously, these techniques could not have been combined because the use of the corneal reflex to measure eye position requires both eyes to be uncovered. However, to measure the full deviation of an eye, one eye must be covered or binocular vision disturbed in some other way. This is generally achieved using the alternate prism cover test which allows the measurement of the combination of the manifest and latent components of the squint. The prism cover test is provided as standard in a clinical assessment of squints, monitoring patient progress and planning surgical intervention. However, this test is not suitable for use and is difficult to accurately measure in young children or in patients of any age with vision in one eye.

The present invention overcomes these disadvantages and allows a clinician to perform a range of corneal reflex measurements by position. In particular, the present invention allows a clinician to perform an equivalent test to the prism cover test wherein the combination of the manifest and latent components of a squint can be measured.

Hence a major advantage of the present invention is that it allows all the tests described above, i.e. the Hirschberg test, the Prism reflection test and the Krimsky test, to be performed with the additional advantage that the full deviation of the eye can be measured with one eye covered. The manifest and latent components of a strabismus can be measured using the system of the present invention.

Generally, it is the first Purkinje image that is measured by the present invention.

A yet another advantage of the present invention is that it can also be performed in young children, as little cooperation is required.

Furthermore, the test can allow accurate measurements in subjects with poor fixation in one eye.

According to one embodiment of the present invention, the occluder comprises a handle and an occluding head connected to the handle wherein the occluding head is visually opaque and infrared light transmitting.

Preferably, the occluding head is of a size effective to occlude vision of a fixation target through one eye of a patient.

Alternatively, the occluding head comprises an infrared long-pass filter or band.

Optionally, the occluder may comprise an infrared transmitting prism or infrared transmitting prism bar.

According to one embodiment of the invention, the infrared light source and infrared imaging device may be head-mounted. The infrared light source and infrared imaging device may be located in one device.

The infrared imaging device may comprise an infrared sensitive video camera and a head mounted monocular/binocular display to provide immediate feedback of the position and/or deviation of the eyes.

Alternatively, the infrared imaging device may comprise an infrared sensitive video camera and a device for capturing a photographic, video or digital image of the one and/or both eyes of a subject when covered by the occluder.

Ideally, the infrared sensitive video camera is connected to a computer or other recording device to display or record the corneal reflections to allow automated measurements of the eye from image analysis of the corneal reflection position relative to the pupil and/or margins of the cornea. This allows automated measurements to be displayed on the head mounted monocular/binocular display.

According to another embodiment of the invention, the system comprises an infrared image intensifier which amplifies the infrared light and converts the infrared light to visible wavelengths to allow detection by the human eye.

The present invention also provides a method for observing movement and measuring deviations of an eye using corneal reflex measurements comprising the steps of:

a. Directing an infrared light source toward the eye of a subject while the subject looks at a fixation target and wherein the infrared source is aligned or adjacent to the fixation target;

b. Covering one eye of the subject with a hand held visually opaque infrared transmitting occluder;

c. Observing the changes in the deviation of the occluded eye through the visually opaque infrared transmitting occluder via an infrared imaging device and/or recordal of these changes.

Preferably, the method involves obtaining an image of each eye covered and both eyes uncovered.

As above, the Hirschberg test, Prism reflection test and Krimsky test may be carried out using this method. Furthermore, the measurement of manifest and/or latent strabismus is also possible.

As with previous embodiments, the infrared imaging device may comprise an infrared sensitive video camera and a head mounted monocular/binocular display allows immediate feedback of the deviation of the eyes to be obtained. Alternatively, the infrared sensitive video camera may be connected to a computer or other recording device to display or record the corneal reflections to allow automated measurements of the eye from image analysis of the corneal reflection position relative to the pupil and/or margins of the cornea.

The provision of automated measurements which are displayed on the head mounted monocular/binocular display allows the simultaneous clinical examination and assessment of measurements of eye position.

According to a further embodiment of the invention, there is provided a method for screening for visual abnormalities in a group of subjects using the method according to the present invention further comprising the steps of obtaining multiple images of the eyes of each subject for analysis at the time of examination and/or for later review. In this embodiment, three images of the eyes of each subject are taken comprising an image of each eye covered and both eyes uncovered.

According to yet another aspect of this invention, there is provided a visually opaque hand held eye occluder which transmits infrared light and occludes vision through an eye of a subject.

Preferably, the occluder comprises a handle and an occluding head connected to the handle wherein the occluding head is visually opaque and infrared light transmitting and is of a size effective to occlude vision of one eye of a patient.

Alternatively, the occluding head comprises an infrared long-pass filter or band.

Optionally, the occluder or occluding head comprises a prism or prism bar. Yet another alternative is that the occluder is a visually opaque infrared transmitting prism or visually opaque infrared transmitting prism bar. The visually opaque IR transmitting prism bar comprises a frame and a series of graduated prisms. The prism and/or frame may be made of IR transmitting visually opaque material.

Preferably, the occluder handle may be made of visually opaque infrared transmitting material. Alternatively, the occluder handle may be made of any other plastics material with the proviso that the occluding head is made entirely or partly of visually opaque infrared transmitting material. It will be understood that the occluder may be made of any plastics material wherein the occluding head comprises and infrared long pass filter or band pass filter Ideally, the occluder is from approximately 3 to 4 mm in thickness although other constructions are contemplated.

Preferably, the occluder and/or occluding head is made of acrylic, preferably PSC-S306™.

The embodiments of the present invention will be described in detail with reference to the accompanying drawings.

Figure 4A:
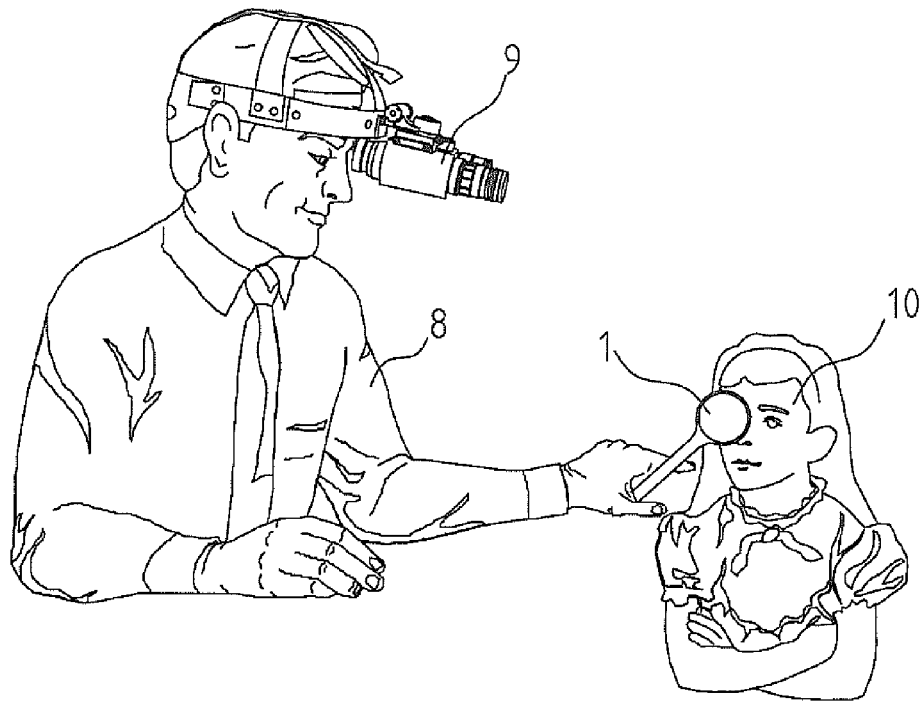
Figure 4B:
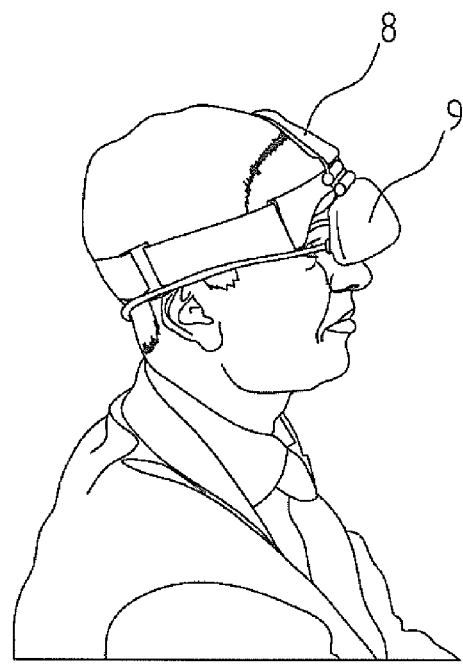
Figure 5:
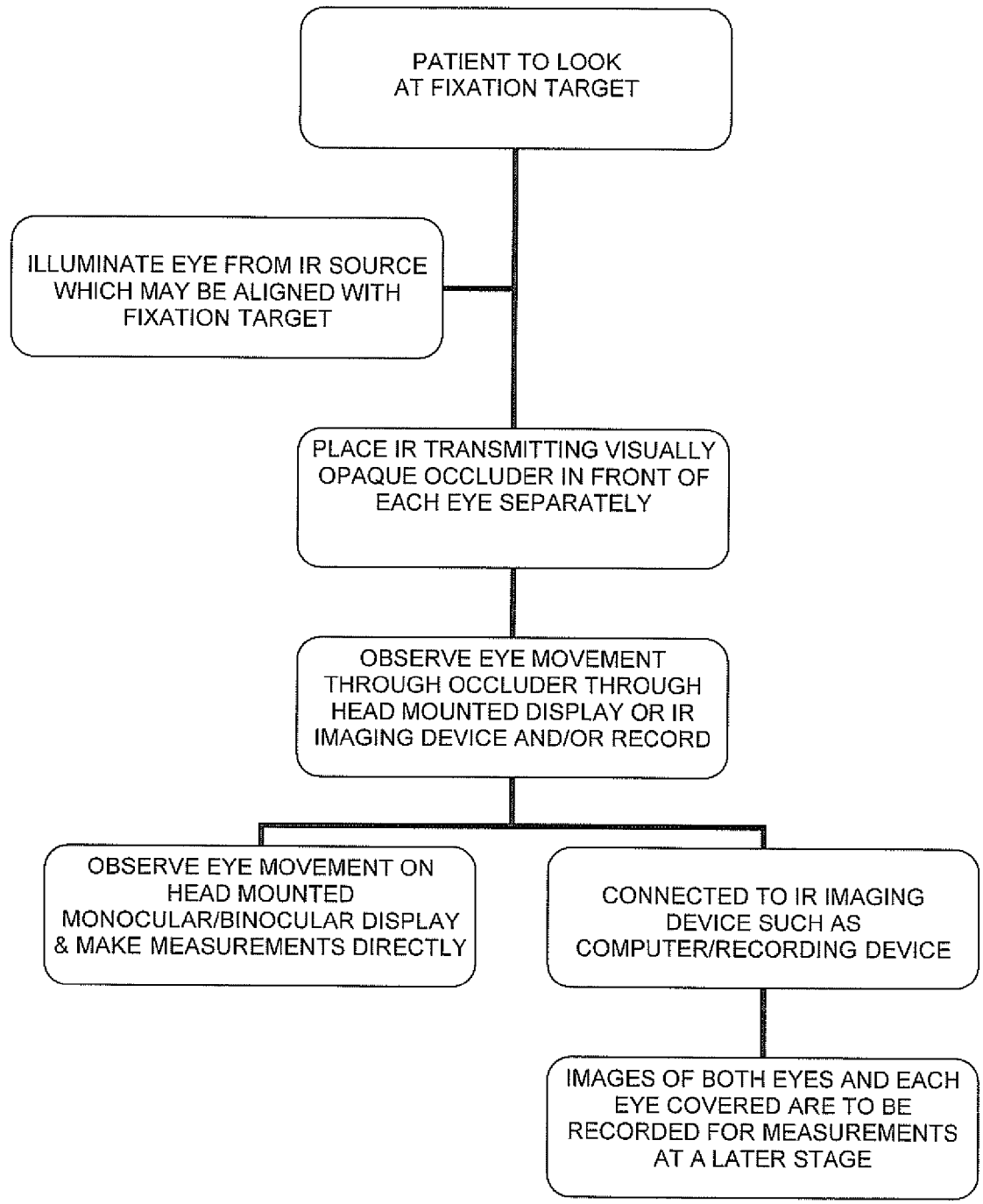
Figure 6A:
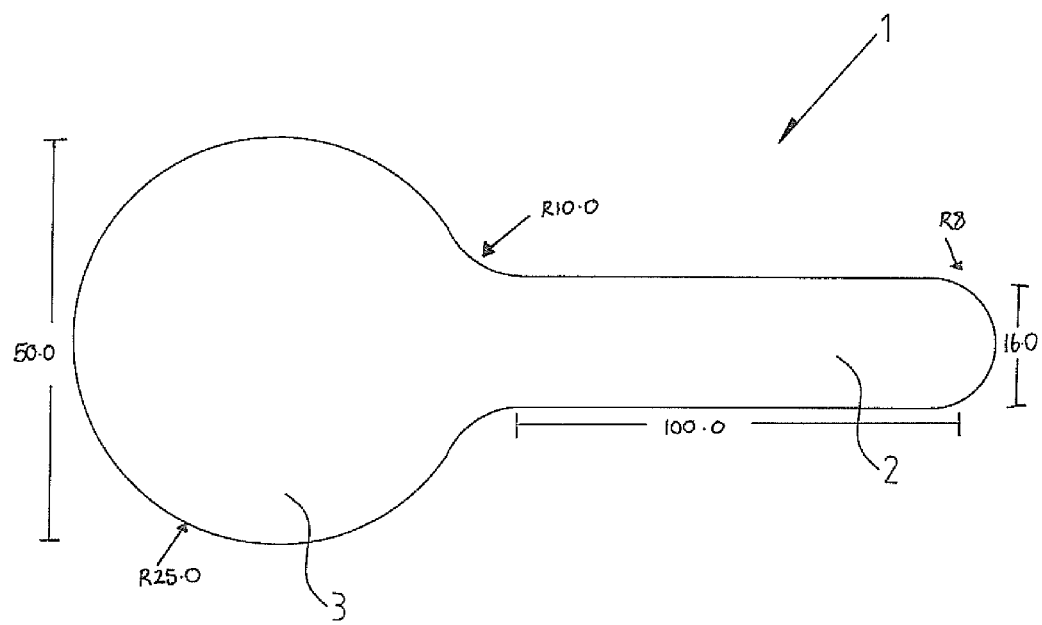
Figure 6B:
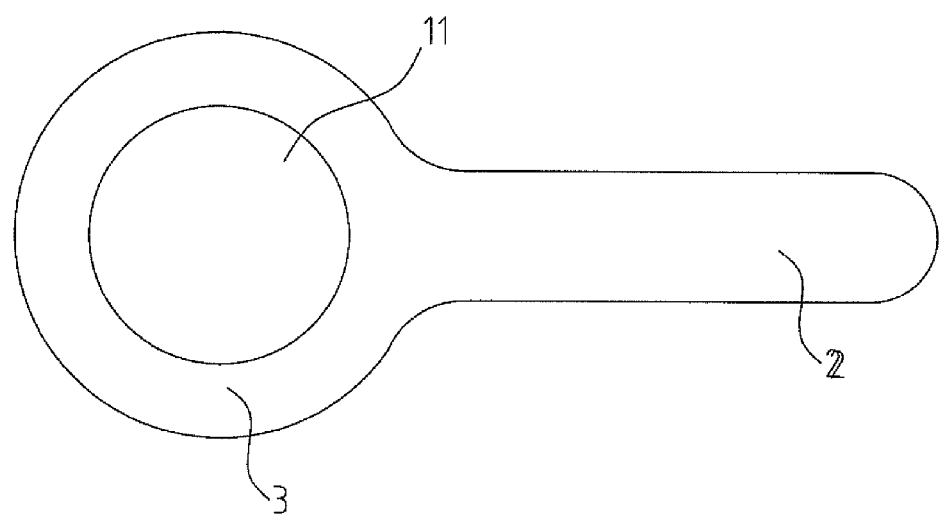

FIG. 4*a* shows a perspective view of the invention in use showing an observer with a head mounted monocular IR imaging device and a subject opposite;

FIG. 4*b* shows a perspective view of a head mounted binocular IR imaging device;

FIG. 5 is an illustrative flowchart of how the system of the invention operates in practice; and FIGS. 6*a* and 6*b* shows illustrative figures of further occluders which may be used according to the invention.

Essentially, there are three elements of the present invention. The first element is a handheld eye occluder which is visually opaque and infrared transmitting. The second element of the system is an infrared light which will pass through the eye occluder and the resulting reflections from the eye pass back to an observer and can be observed through the third element of the system which comprises an infra-red imaging device. It will be envisaged that the second and third elements of the system can be combined into one device. Further details of each element of this system follow.

Figure 1:
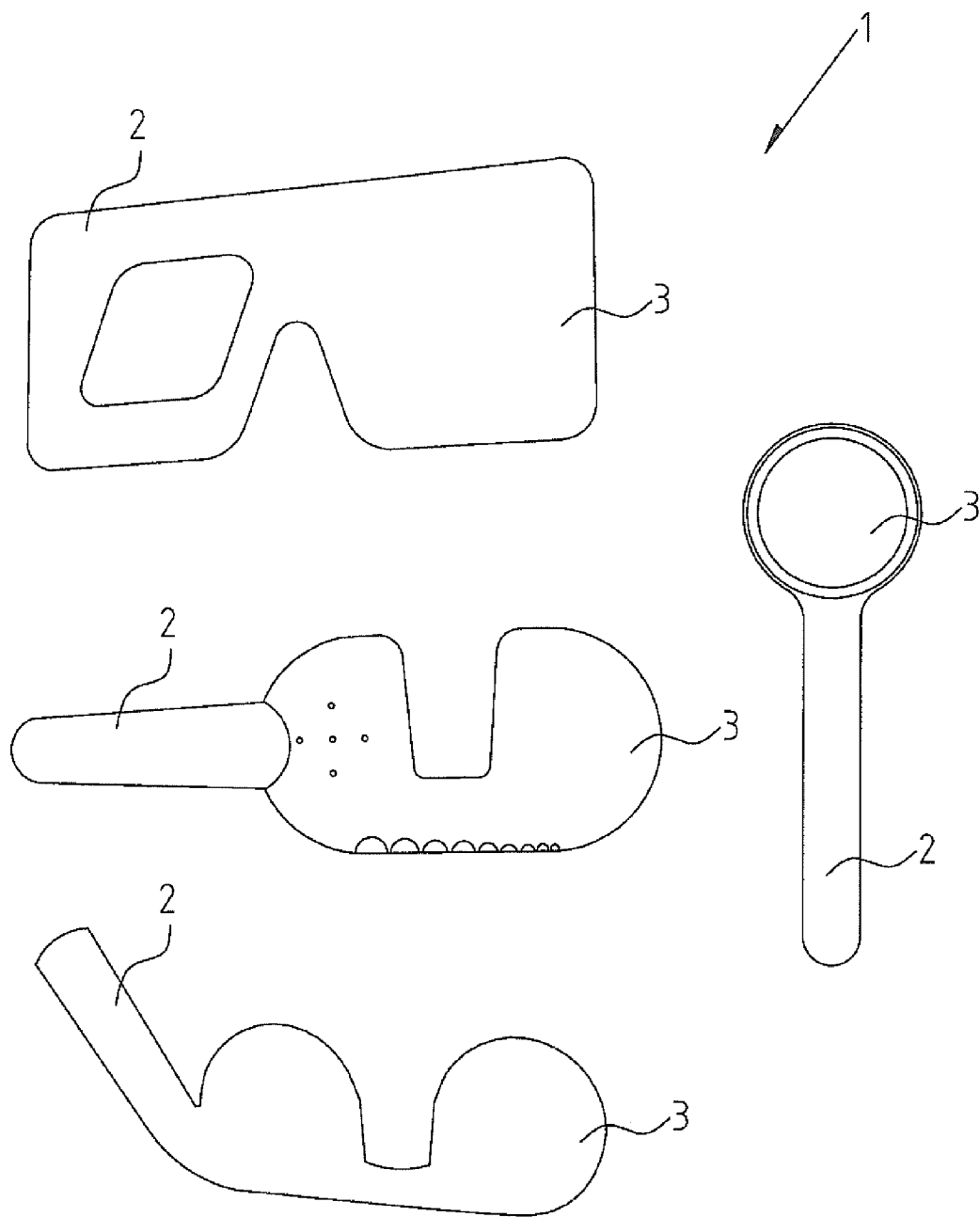
FIG. 1 shows an illustrative figure of several conventional occluders which may be used according to the present invention.
Figure 3:
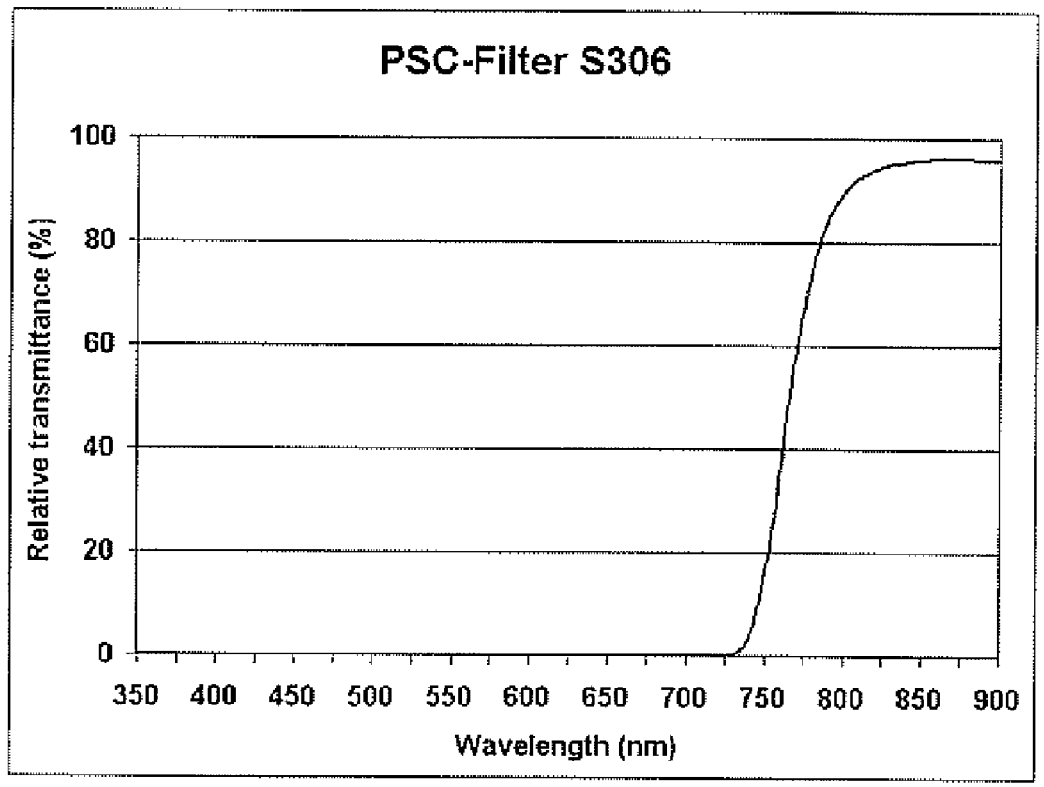
FIG. 3 is a graph of the optical properties of Acrylic PSC-306™ which is suitable for use in the present invention.

In one preferred embodiment of the invention, as shown in FIG. 1, the first element of the system is small handheld occluder (1) similar in shape to existing occluders but with the special optical property of being an infrared pass filter. This can be achieved by using a specialised plastic such as acrylic PSC-S306™ which has the optical property of absorbing visible light but letting infrared light pass almost unhindered (see FIG. 3). This plastic looks black and if sufficiently thick (3-4 mm) prevents all vision.

Various conventional constructions of occluders may be contemplated. These are shown in FIG. 1. The important aspect is that each occluder has a handle (2), i.e. an area of any shape that enables the device to be hand held, and an occluding head (3), which is of sufficient size to occlude vision from an eye of a subject.

Alternatively, rather than using an infrared transmitting plastic to produce the entire occluder, it is also be possible to make the occluder handle (2) from any material and incorporate a small infrared long pass or band pass filter which could be plastic, glass or any suitable filter material (not shown) into the occluder head (3). The infrared long pass or band pass filter may comprise part of or comprise the entire occluding head (3). It will be understood that the infrared long pass of band pass filter must be of sufficient size to occlude vision from an eye of a subject. Thus, it is contemplated that the filter area can be smaller than the occluding head (3) if the head is made from more than one material. However, the central filter (11) size must be sufficient to easily visualize the entire cornea, typically from approximately 12 to approximately 70 mm (see FIG. 6b)

Infrared filters, which are broadband filters, absorbed the entire visual spectral phase and provide the maximum transmittance for displays with near infrared wavelengths. A bandpass filter is a device that passes frequencies within a certain range and rejects frequencies outside that range. Specifically, long pass filters and short pass filters are interference filters which provide a sharp cut-off either above or below a particular wavelength. In the case of long pass filters, the transmitted wavelength is long wavelength radiation, while the short wavelength is reflected. Generally, such long pass filters are constructed of hard durable surface materials covered by electric coatings.

In addition as this device will normally be used with prisms to facilitate manual measurements, it is be possible to combine the occluder and prisms into one device and have infrared transmitting (but visible wavelength blocking) prisms or an infrared transmitting (but visible wavelength blocking) prism bar. Thus, the occluder may be dispensed with and the prisms may be used for both measurement and occlusion.

Figure 2:
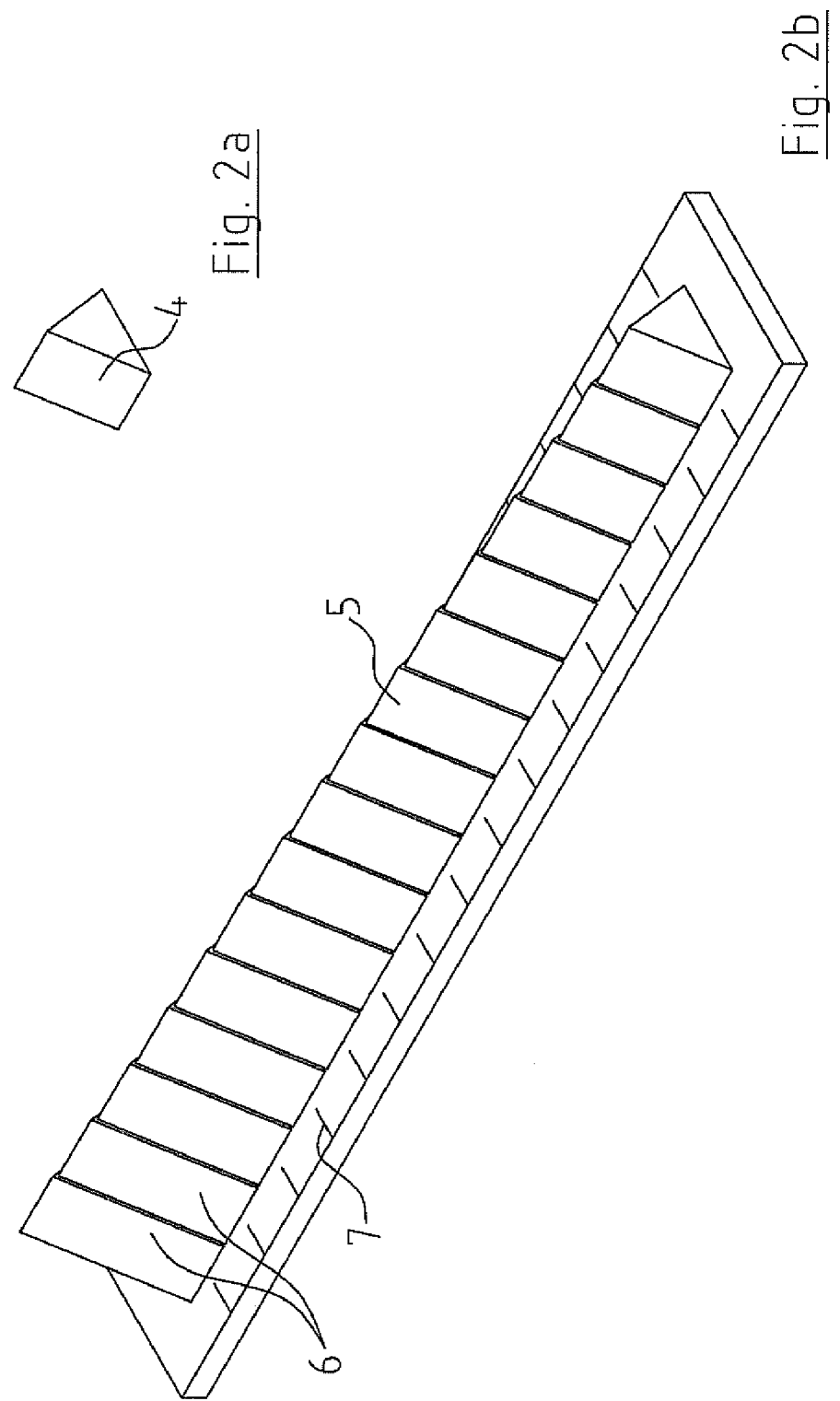
FIG. 2 shows an illustrative figure of a prism and prism bar which also may be used according to the present invention.

A typical optical prism (4) and prism bar (5) are shown in FIG. 2. The prism bar is essentially a graduated series of prisms (6) of different strengths mounted on a frame (7). Typically, the frame is a ruler type device. The frame (7) only may be made of visually opaque and infrared transmitting material and a conventional prism bar is then attached to the frame. Alternatively, both the frame (7) and the prism bar (6) may be made from visually opaque and infrared transmitting material. Thus, a one or two piece construction may be envisaged.

The second element of the system, an infrared light will however pass through the occluder (conventional occluder shape or prsim/prism bar) and the resulting reflections from the eye pass back to an observer.

The third element of the system comprises an infra-red imaging device such as an infra-red sensitive video camera and a small head mounted monocular or binocular display. This allows the observer to view the infrared image in visible light. The head mounted apparatus allows the observer's hands to remain free to facilitate the ocular examination with the aid of the infra-red transmitting occluder and prisms.

FIG. 4a shows the three elements of the system in use with a monocular IR imaging device, FIG. 4b shows a binocular IR imaging device and FIG. 5 provides a general flowchart of the steps involved in the method of the invention.

In FIG. 4a, there is shown an observer (8) wearing a head mounted monocular or binocular IR display (9). This may be connected to an IR imaging device for recordal of the images observed.

The subject (10) fixes on a distant fixation target (not shown). The eye of the patient (10) is illuminated from the IR source which may be aligned with the fixation target. In use, the observer (8) holds the hand held visually opaque IR transmitting eye occluder (1) in front of the eye of a subject (10). The movement of the eye is observed through the head mounted display or IR imaging device (9). The observer (8) may either make observations and measurements directly or if the IR imaging device is connected to a computer, the images of both eye and each eyes covered may be recorded for measurements at a later stage.

The fixation point (target), camera viewing and infrared illumination should ideally be co-aligned. This can be achieved with the use of prisms, pellicle beam splits, dichroic mirrors or partially silvered mirrors but in practical terms will be adequately achieved by alignment within a few millimetres. The fixation point may be mounted on the infrared imaging device along with the infrared illuminators (eg the IR emitting LEDs) or these components may be on separate devices with the operator aligning them manually. As one hand would normally be holding the IR transmitting visually opaque occluder, the other can only reasonably hold a fixation target or a combined fixation target and IR illuminator. Good alignment of the IR illumination and camera is important not only for accuracy of measurements but also illumination of the pupil, the pupil appearing brightest when the camera and IR illuminator are aligned.

The IR imaging device may be a conventional night vision device, either monocular or binocular display. It may also be adapted for use with this invention. For example, an additional IR filter may be present over the IR imaging device. In addition, the night vision/infrared device is adapted for use as a head mounted device to allow hands free viewing. This is shown in FIGS. 4a and 4b as the arrangement of straps which are attached to the night vision device which enables it to be head mounted and allow the observer free hand movement. Alternatively, the IR imaging device may be mounted on a helmet or any other device which fits over and observers head to allow hands free viewing. In addition, the IR imaging device may be mounted on a pair of goggles which fits over the wearers eyes. The IR imaging device may be arranged to flip-up to make it unnecessary to remove the goggles completely from the head each time.

Most infrared imaging systems are designed for imaging objects at a greater distance than appropriate for this application. The present invention generally operates within a range of from approximately 50 cm to 100 cm (depending on a practitioners normal examination habits and arm length) whereas night imaging systems are usually intended for distances of several meters and greater. This results in standard imaging systems having high power infrared illumination and a focussing range which does not encompass the small distances involved in eye examinations. For the present invention, the illumination provided by the infrared source must be reduced to safe limits for the human eye at the operating distance. These limits are covered by US and European safety standards e.g. the American National Standards Institute (ANSI) Z136-1-1993 and European Standard EN 60825-1 1994-1996. Safe exposure limits require a reduction in infrared illumination intensity as a function of distance with a relationship corresponding to an inverse square relationship.

The focussing requirements for the required close working range may also require a modification of standard infrared imaging devices which may include the replacement of the imaging lens of the imaging device.

For infrared imaging devices based on ccd (charge coupled device) cameras, it may be beneficial to provide an infrared pass filter in front of the camera lens if the testing environment is expected to be bright. If there is a lot of ambient visible light the automatic gain control in most ccd cameras may reduce the sensitivity in the infrared to such a degree that the eye cannot be imaged through the infrared pass opaque occluder. The provision of an infrared filter in front of the camera ensures that the gain control is well matched to the infrared illumination rather than the visible light illumination.

In a preferred embodiment, in order to maximize accuracy the video camera also has a zoom or magnifying capability.

In another embodiment, the video signal can be connected to a computer or other recording device to allow automated analysis of the corneal reflection positions either during the exam or at a later time. This latter capability provides a mechanism whereby the examination could be performed by a technician with basic training but the analysis which requires more skill and experience is performed later, for example when the technician returns from a school visit back to a hospital clinic.

According to one embodiment, in this type of screening application, the invention would minimally require the use of a visually opaque infra-red transmitting occluder that is held over one eye, an infra-red light source and a device for capturing a photographic, video or digital image of the two eyes. An image or images would be captured with both eyes uncovered and each eye covered in turn for later analysis. These images would allow the diagnosis of manifest and latent squints making the device suitable for use in a school or community based vision screening programme.

In the case of computer assisted analysis of corneal reflections the results may be displayed on a separate monitor or fed back (by cable or wirelessly) to the head mounted display so the observer could have immediate feedback of the measured deviation of the eyes while conducting an examination.

When making measurements for distant fixation targets the observer has two choices. Firstly, to have a distant infra-red light source combined with a distant fixation target or to use a distant fixation target and the head mounted infrared source. In the former case measurements can be made in exactly the same way as for near targets and a switch needs to be incorporated to turn off the head mounted infrared light source(s) to avoid any confusion as to the correct corneal reflection. In the latter case a correction needs to be made for the distance between the near infrared light source and the distant fixation target as under these the conditions the covered eye will appear to slightly turned in by an amount equal to this correction factor. This correction is a matter of trigonometric calculation the angular difference being given by the following equation:

$$\text{Correction} = \arctan(\text{IOS}/\text{IRD}) - \arctan(\text{IOS}/\text{DFD})$$

where IOS=intraocular separation, IRD=infrared light source distance and DFD=distant fixation distance.

The use of an infrared camera and head mounted display is a cost effective means of providing an observer with real-time imaging of infra-red light but other technologies would also be suitable such as night vision image intensifiers which amplify infra-red light and convert it to visible wavelengths detectable by the human eye.

FIGS. 6a and 6b shows illustrative figures of further occluders (1) which may be used according to the invention. FIG. 6a gives the typical dimensions (in mm) of a conventional occluder (1) which may be used in the present invention. The occluder handle (2) and head (3) may be made of visually opaque IR transmitting material. Alternatively, the occluding head (3) only may be made of visually opaque IR transmitting material. FIG. 6b shows an alternative construction, where the handle (2) and head (3) can be made from any material, usually a plastic material and the head (3) comprises a small visually opaque IR transmitting material area (11) located within the head of sufficient size to occlude vision from one eye of a subject. This area (11) may comprise an IR long pass filter, band pass filter or prism/prism bar of any suitable shape.

It will be understood that the present invention is not limited to the embodiments hereinbefore described.

The invention claimed is:

1. A method for observing movement and measuring deviations of an eye using corneal reflex measurements comprising the steps of:
   a. Directing an infrared light source toward the eye of a subject while the subject looks at a fixation target and wherein the infrared source is aligned or adjacent to the fixation target;
   b. Covering one eye of the subject with a hand held visually opaque infrared transmitting occluder comprising a handle and an occluding head connected to the handle wherein the occluding head is of a size effective to occlude vision of a fixation target through one eye of a subject; and
   c. Observing the changes in the deviation of the occluded eye through the visually opaque infrared transmitting occluder via an infrared imaging device and/or recordal of these changes, wherein the occluder, during observing, transmits infrared light and blocks visible light.

2. The method of claim 1 wherein an image of each eye covered and both eyes uncovered is obtained.

3. The method of claim 1 wherein the first Purkinje image is measured.

4. The method of claim 1 wherein the Hirschberg test, the Prism reflection test and/or the Krimsky test are carried out.

5. The method of claim 4 for the measurement of manifest and/or latent strabismus.

6. The method of claim 1 wherein the infrared light source and infrared imaging device are head mounted, the infrared imaging device comprises an infrared sensitive video camera and a head mounted monocular/binocular display to provide immediate feedback of the deviation of the eyes.

7. The method of claim 1 wherein the infrared imaging device comprises an infrared sensitive video camera and a device for capturing a photographic, video or digital image of the eyes.

8. The method of claim 7 wherein the infrared sensitive video camera is connected to a computer or other recording device to display or record the corneal reflections to allow automated measurements of the eye from image analysis of the corneal reflection position relative to the pupil and/or margins of the cornea.

9. The method of claim 7 wherein the automated measurements are displayed on the head mounted monocular/binocular display to allow simultaneous clinical examination and assessment of measurements of eye position.

10. The method of claim 1 wherein the infrared imaging device comprises an infrared image intensifier which amplifies the infrared light and converts the infrared light to visible wavelengths to allow detection by the human eye.

11. A method for screening for visual abnormalities in a group of subjects using the method of claim 1 comprising the further step of obtaining multiple images of the eyes of each subject for analysis at the time of examination and/or for later review.

12. The method of claim 11 wherein three images of the eyes of each subject are taken comprising an image of each eye covered and both eyes uncovered.

13. The method of claim 1 wherein no equipment is mounted on the subject.

14. The method of claim 1 wherein changes in the deviation of the occluded eye are observed via the infrared imaging device, and the infrared light source and the infrared imaging device are located away from the subject.

15. The method of claim 14 wherein the infrared light source and the infrared imaging device are mounted on a person performing the observing of changes in the deviation of the subject's occluded eye.

16. The method of claim 15, wherein the observer is positioned approximately 50 cm to 100 cm away from the subject.

17. A method of using the system of claim 15 to measure deviations of an eye using corneal reflex measurements of a fixation target comprising the steps:
    directing the infrared light source toward the eye of a subject while the subject looks at the fixation target;
    occluding the eye with the eye occluder;
    with the infrared imaging device, observing the changes in the deviation of the occluded eye through the occluder.

18. A system for measuring deviations of an eye using corneal reflex measurements of a fixation target wherein the system comprises
   a. An infrared light source aligned with or adjacent to a fixation target;
   b. A hand held visually opaque infrared light transmitting eye occluder wherein the occluder comprises a handle and an occluding head connected to the handle wherein the occluding head is visually opaque and infrared light transmitting and the occluding head is of a size effective to occlude vision of a fixation target through one eye of a subject; and
   c. An infrared imaging device to observe and/or record the eye and corneal reflex measurements, wherein the occluder, during observing, transmits infrared light and blocks visible light.

19. The system of claim 18 wherein the occluding head comprises an infrared long-pass filter or band and/or an infrared transmitting prism or infrared transmitting prism bar.

20. The system of claim 18 wherein (a) and/or (c) are head-mounted.

21. A system for measuring deviations of a subject's eye using corneal reflex measurements of a fixation target wherein the system comprises:
    an infrared light source;
    an eye occluder sized and shaped to occlude the subject's view of the fixation target from one eye, wherein the occluder transmits infrared light but is opaque to visual light; and
    an infrared imaging device that images the subject's eye through the occluder.

* * * * *